(12) United States Patent
Dias et al.

(10) Patent No.: US 6,190,323 B1
(45) Date of Patent: Feb. 20, 2001

(54) DIRECT CONTACT SCANNER AND RELATED METHOD

(75) Inventors: J. Fleming Dias, Palo Alto; Hewlett E. Melton, Jr., Sunnyvale, both of CA (US)

(73) Assignee: Agielnt Technologies, Palo Alto, CA (US)

( * ) Notice: Under 35 U.S.C. 154(b), the term of this patent shall be extended for 0 days.

(21) Appl. No.: 08/614,572

(22) Filed: Mar. 13, 1996

(51) Int. Cl.[7] ........................................... A61B 8/00
(52) U.S. Cl. ................................................. 600/446
(58) Field of Search .................... 600/459, 446, 600/466–471; 310/328, 334; 333/154, 141

(56) References Cited

U.S. PATENT DOCUMENTS

| | | | |
|---|---|---|---|
| 4,590,803 | 5/1986 | Harrold | 73/590 |
| 4,671,292 | * 6/1987 | Matzuk | 128/660.1 |
| 4,742,318 | 5/1988 | Jen et al. | 333/141 |
| 5,271,402 | * 12/1993 | Yeung et al. | 128/660.1 |
| 5,284,148 | * 2/1994 | Dias et al. | 128/662.06 |
| 5,291,090 | 3/1994 | Dias | 310/334 |
| 5,507,294 | * 4/1996 | Lum et al. | 128/662.06 |

FOREIGN PATENT DOCUMENTS

0580304 A1   7/1993   (JP) ................... A61B/8/12

\* cited by examiner

Primary Examiner—Francis J. Jaworski

(57) ABSTRACT

A direct contact scanner uses a fiber acoustic waveguide to convey ultrasound from an ultrasound transducer to a direct contact area. The waveguide extends from a main body of the scanner into an oblong nose, and terminates in a deflector. To minimize thickness of the nose, the waveguide and deflector are rotated about an ultrasound transmission axis of the waveguide, enabling the scanner to be used in a variety of situations where quarters are cramped. A coupling fluid conveys ultrasound between the deflector and a radome, which directly contacts the object to be scanned. Using the waveguide, an ultrasound transducer and supporting electronics may be distanced from the direct contact area and separated from the fluid, thereby insulating the fluid from possible electronic leakage currents and heat.

21 Claims, 3 Drawing Sheets

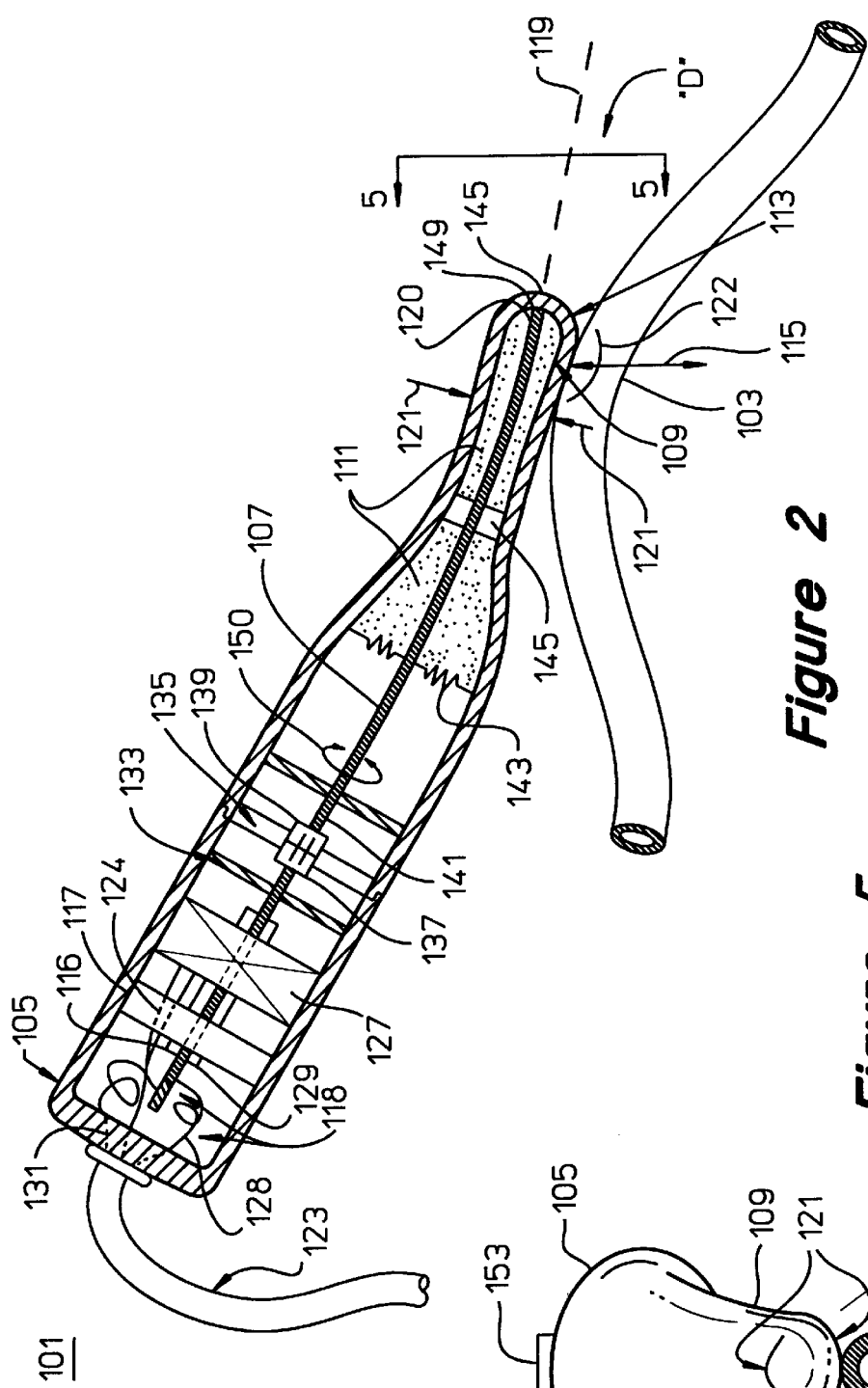

DIRECT CONTACT SCANNER AND RELATED METHOD

The present invention relates to a direct contact scanner. More particularly, it provides a novel hand-held probe that can be used in a wide variety of imaging applications, including invasive intraoperative surgical applications.

BACKGROUND

Open heart surgery is sometimes used to clear stenosed artery segments which are in close proximity to the heart. It is not uncommon during this procedure for surgeons to literally feel arterial segments with their fingers to locate hard segments (a process known as "palpation"), and in that way establish and localize a stenotic segment of the artery. While well-trained and experienced surgeons are typically adept at this task, the potential for uncertainty and error exists.

Recently, some hospitals have begun to develop direct contact scanners that use ultrasound to image areas of the body. Scanners of this type are typically used for non-invasive procedures, for example, in obstetrics. In operation, these devices direct ultrasound into the body, with various body tissues producing ultrasound echoes which are detected by the scanner and electronically used to construct an image. These scanners have proven very useful in obtaining images of certain internal body tissues, though their resolution of deep or intricate tissues is limited, and they are not readily applied to invasive situations.

A typical scanner 11 is seen in FIG. 1. The scanner includes a main scanner body 13, and a radome 15 that directly contacts an object 17 to be scanned (the human body). The radome 15 also houses a coupling fluid 19 which is used to help transmit ultrasound. As used herein, "radome" is a surface that is transparent to the imaging waves used to scan the object 17, such as an acoustically transparent window. The coupling fluid 19 is necessary in the case of ultrasound, because it permits scanning movement of an ultrasound transducer 21, as indicated by reference arrow 23, and because high frequency ultrasound does not transmit well in air.

Within the radome 15 and the coupling fluid 19, the scanner 11 includes a transducer assembly 27, consisting substantially of the transducer 21 (a directional ultrasound transducer operating in the range of 2.5 to 10.0 megahertz) and a pivotal support 29 for the transducer. The pivotal support enables the transducer to be pivoted such that the direction of produced ultrasound sweeps through a sector, as indicated by reference arrow 31, causing ultrasound to image a plane or section of object 17 to be scanned. The transducer 21 has insulated electric leads 32 which are connected to processing circuits (not shown) in the main scanner body 13. These processing circuits control the transducer to both produce ultrasound in discrete bursts, and also to detect ultrasound echoes and responsively generate an image. Typically, the leads 32 supply an excitation signal to the transducer which is on the order of 100 volts. An angle encoder 33 in the main scanner body generates a sync signal that informs the main processing unit as to the beginning of a new image frame. The transducer is moved by a reciprocating motor 35, located in the main scanner body, which pulls a belt 37 back-and-forth to pivot the transducer through the sector. The belt wraps around a pulley 39 of the transducer and is, in turn, anchored to the main body by a spring 41 and a fixed support 43.

While generally useful for non-invasive applications, such as obstetrics, cardiology and the like, direct contact scanners of the type just described have a number of shortcomings. In particular, these shortcomings make it impractical to use the scanners in invasive surgical procedures, for example, open heart surgery, or in a wide variety of other applications.

First, the transducer and its electrical leads are typically located within the coupling fluid, in order that ultrasound can be directly coupled to the object to be scanned while the transducer is being pivoted. However, this construction generally requires the use of electric potentials immediately adjacent to the radome, in close proximity to body tissues, which presents a danger of electrical leakage during surgery. This danger is particular acute if the scanner will be used near highly sensitive tissues, for example, the heart or brain.

Second, the size of the probe required to house the transducer and pivotal mounting in close proximity to the radome makes a direct contact area of the probe excessively large, rendering it difficult to use the probe in hard-to-access areas within the body cavity during surgery. For example, during brain surgery, it might be desirable to use a direct contact scanner through a bore hole in the skull to image a tumor; the typical scanner just described presents a direct contact area which is generally too large to be usable in these situations. This difficulty renders the scanners unusable for many invasive applications, as well as for most non-medical applications where quarters are cramped.

A third, related problem, is that the frequencies of ultrasound producible by the scanner just described are limited; since frequency of ultrasound produced is inversely proportional to transducer thickness (transducer material generally must be about one-half wavelength thick, given the desired frequency's speed of travel in the transducer material), high frequency transducers are relatively thin and more prone to damage where a moving transducer assembly is utilized. Generally, use of a moving transducer assembly requires use of a thick solid backing for high frequency transducers, which unfortunately imposes undesired weighting and high inertia considerations at the direct contact end of the scanner. This arrangement is undesirable, and it in practice limits the range of ultrasound frequencies that are produced by the scanner. In turn, limitation in the range of ultrasound frequencies places a limitation on the resolution that can be achieved with the scanner. To be able to properly diagnose the nature of a tumor or an occlusion in a blood vessel such as a coronary artery, it would be extremely useful to be able to characterize these tissues or lesions in extreme detail, which is generally achievable using ultrasound frequencies in the range of thirty- to fifty-megahertz, and perhaps higher.

There is a dire need for a method or device for safely imaging body tissues, particularly during surgery, which does not mandate reliance upon a surgeon and which does not expose a patient to leakage currents. Such a method or device should require only a small contact area such that it is usable in remote areas, for example, in body tissue areas such as the brain that are not easily accessed. Preferably, such a method or device should offer a precise, high-resolution imaging procedure, to enable quick diagnosis of maladies with a high degree of accuracy. Also, it would serve the physician well if the operating frequency of a scanner could be changed while the scanning is in progress. Finally, because of the requirement of disposableness due to fear of contagion, the device or method should use inexpensive, easily assembled parts which may replaced as necessary, which would also enable the use of interchangeable parts to adapt the scanner to different applications. The present invention solves these needs and provides further related advantages.

SUMMARY

The present invention provides a novel hand-held scanner that is safer, and can be used in invasive surgical applications. As a result, it provides an imaging tool that assists a surgeon in real time during a surgical process, and that does not require a surgeon to physically feel by hand internal body tissues. Still further, the present invention provides a direct contact scanner with reduced risk of leakage currents and reduced risk of exposure to contagion. The present invention places imaging equipment away from a direct contact area, and as a result, the scanner of the present invention utilizes a relatively small direct contact area. This facilitates use of the scanner in remote areas, thereby providing a means of safely imaging tumors and other sensitive body tissues during surgery. In addition, the provision of a narrow direct contact area enables the scanner to be adapted to a wide variety of applications outside the field of medicine.

In accordance with the principles of the present invention, the novel scanner includes a transducer that transduces electronic signals and imaging waves; this transducer can be electromagnetic, sonic, or any type of transducer that generates imaging waves in response to an electronic signal, or that detects such waves. The scanner also has a scanner surface that directly contacts an object to be scanned. This scanner surface, or "radome," is made of a material chosen to be transparent to the imaging waves, and it is positioned between the transducer and the object. In between the scanner surface and the transducer is a coupling media having good transmission characteristics for the imaging waves (whether ultrasound, light, microwave, etc.). The coupling media can be air, water, or any other substance with good transmission characteristics for the imaging waves chosen, such that the waves are not attenuated substantially in between the transducer and an imaging target. Finally, the scanner includes a waveguide for the imaging waves which couples the transducer and the coupling media. The waveguide can be of a practical length or shape necessary to assist conveyance of the imaging waves to the radome. In this manner, the transducer can be positioned away from the radome, in a position that minimizes the danger of leakage currents, and permits a small direct contact area with the object, e.g., since the transducer need not be mounted immediately adjacent to the radome, within a coupling media. The waveguide also permits the coupling media to be distanced from heat-generating and electronic elements, such as electronics in the device, thereby providing heightened accuracy in some imaging applications.

In more particular aspects of the invention, the waveguide includes a deflector (which presents either a mirror or refractor to redirect the imaging waves) mounted by the waveguide. The waveguide preferably is a cladded fiber having a cladding layer that is much greater in diameter than a core layer, for example, four times as thick. The waveguide can be rotated about its longitudinal axis, such that the deflector is rotated at a distal end of the scanner, without requiring a large direct contact area with the imaging target. The deflector is positioned at an angle to the waveguide such that, as the waveguide is oscillated around its longitudinal axis, the imaging waves are distributed radially in a sector through the radome and into the object, with reflections returning along the same path. The waveguide (e.g., a cladded fiber of fused quartz) can be made to be relatively long (as limited by practical loss), and thus, electrical and mechanical parts may be positioned well away from the radome and the direct contact area.

Another form of the invention provides an improvement to ultrasound scanners. This improvement includes the use of a radome to directly contact the object; an ultrasound transmission fluid inside the scanner in direct contact with the radome, the fluid permitting transmission of the ultrasound produced by the transducer toward the radome without substantial attenuation; and, an ultrasound waveguide that couples the transducer to the transmission fluid. As mentioned, this enables a small direct contact area and heightened accuracy in scanning. Moreover, since the ultrasound transducer may be positioned away from the direct contact area, in a hand-held portion of the scanner, a relatively thin (high frequency) transducer may used with a solid backing, as the backing's position in the hand-held portion of the scanner does not undesirably affect weighting or impose difficult inertia considerations. In turn, this construction permits use of relatively high ultrasound frequencies, such as frequencies greater than thirty or fifty megahertz.

Finally, a third form of the invention provides a method of imaging an object using a direct contact scanner, by conveying imaging waves between the coupling media and the imaging mechanism, while isolating the imaging mechanism from direct contact with the coupling media. In invasive surgical procedures, such as open heart surgery, hard-to-access or sensitive tissues may be scanned without exposing those tissues to a surgeon's subjective judgment, and without significant risk of exposure to electric potentials.

The invention may be better understood by referring to the following detailed description, which should be read in conjunction with the accompanying drawings. The detailed description of a particular preferred embodiment, set out below to enable one to build and use one particular implementation of the invention, is not intended to limit the enumerated claims, but to serve as a particular example thereof.

BRIEF DESCRIPTION OF THE DRAWINGS

FIG. 2 is a sideways cross-sectional view of a scanner which embodies the principles of the present invention, used to image an artery.

FIG. 5 is an end view of the scanner of FIG. 2, taken along line 5—5 of FIG. 2.

DETAILED DESCRIPTION

Figure 1:
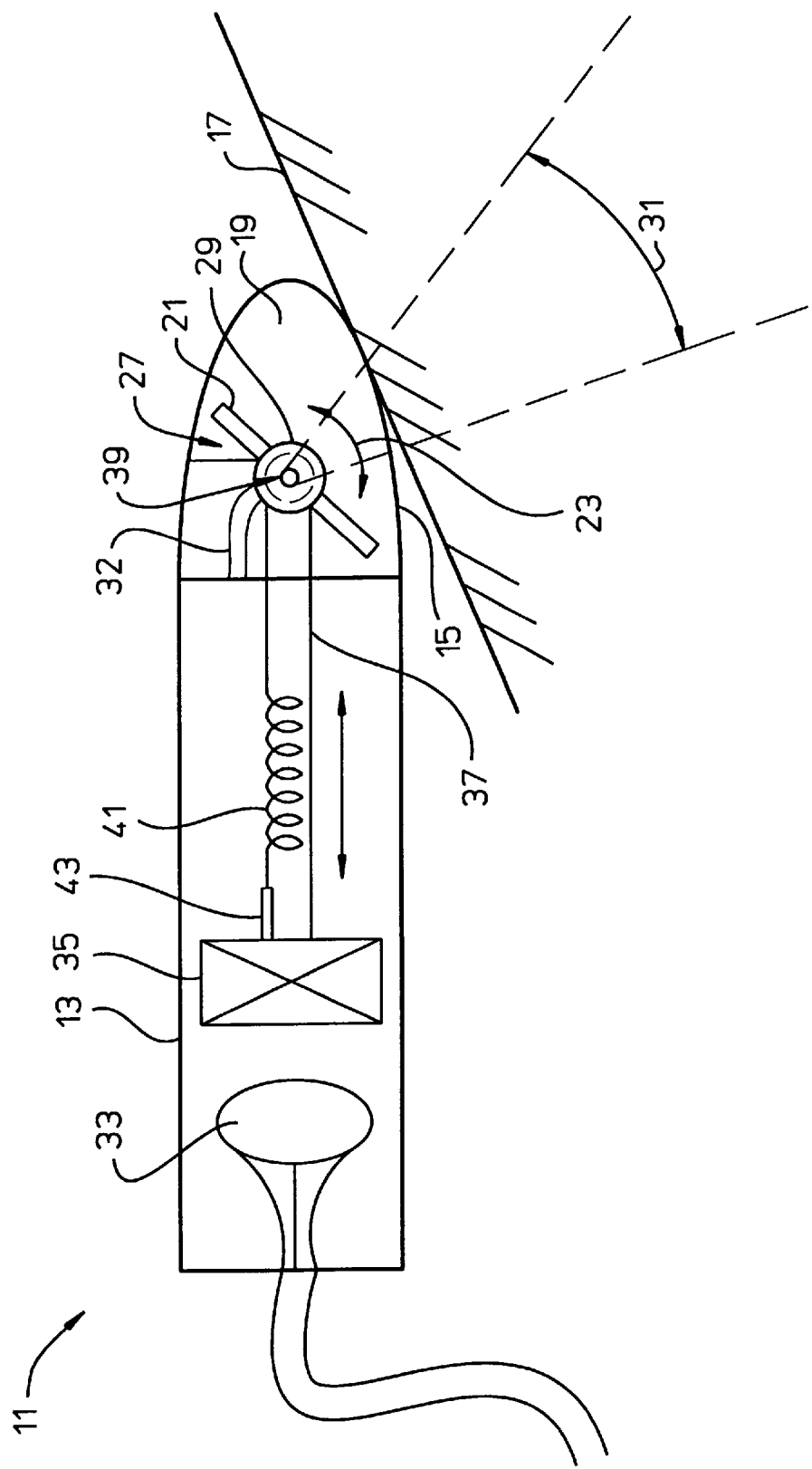
FIG. 1 is a schematic view of a prior art ultrasound scanner, showing a main body and a radome that houses a coupling fluid and a pivotally-mounted transducer.

The invention summarized above and defined by the enumerated claims may be better understood by referring to the following detailed description, which should be read in conjunction with the accompanying drawings. This detailed description of a particular preferred embodiment, set out below to enable one to build and use one particular implementation of the invention, is not intended to limit the enumerated claims, but to serve as a particular example thereof. The particular example set out below is the preferred specific implementation of a direct contact scanner, namely, a hand-held diagnostic probe that uses a fiber acoustic waveguide to provide enhanced ultrasound transmission and a safer probe. The invention, however, may also be applied to other types of systems as well.

As seen in FIG. 2, the preferred embodiment is a handheld probe 101 that scans an object (namely, a stenosed blood vessel during an open heart surgery) 103 by direct contact. All of the electronics 118 of the probe are housed within a cylindrical main body 105 of the probe, and a cladded fiber acoustic waveguide 107 is used to transmit ultrasound between the cylindrical main body 105 and a detachable, oblong nose 109. As with conventional probes, the present probe 101 uses a moving body, a coupling media 111 and a radome 113 to scan the object 103 by direct contact, and also to provide a direct return of reflected imaging waves. Unlike conventional probes, however, the present probe 101 utilizes oscillatory, rotational motion of an ultrasound transducer 117 about a direction of ultrasound transmission. A section 115 of the object 103 which is to be scanned is drawn as a line in FIG. 2, indicating that the direction of scanning is into and out of FIG. 2, in a sense perpendicular to FIG. 2.

The present probe 101 uses ultrasound as the imaging waves and, thus, employs the ultrasonic transducer 117 to generate ultrasound and to detect reflected ultrasound returning from the object 103. In a conventional manner, the probe electronics 118 generates ultrasound for a relatively small period of time, and most of the time controls the transducer 117 to passively detect reflected ultrasound. Preferably, the transducer 117 generates a single ultrasound wave and then, is used to detect reflected ultrasound for period of time sufficiently large to detect any expected reflections before generation of another ultrasound wave in a slightly different direction.

In contradistinction to conventional wisdom, the transducer 117 of the preferred embodiment is mounted within the cylindrical main body 105, well away from the coupling media 111 (a coupling fluid) and the radome 113. In this manner, the coupling media 111 may be insulated from both electric current leakage and heat generation, which can affect accurate ultrasound measurement. Further, the cladded waveguide 107 can be made as long as practical (in terms of minimizing ultrasonic loss), and thus, the cylindrical main body 105 can be very large as compared to the direct contact area 122 of the probe. In this manner, the transducer 117 and any associated backing material may be made relatively large and bulky without imposing undesired weighting or inertia considerations to the direct contact area 122 of the probe.

In this regard, a very narrow direct contact area 122 is achieved by the preferred probe by reciprocally rotating the fiber acoustic waveguide 107 around a longitudinal axis 119, which is also a transmission axis for ultrasound. That is to say, unlike other probe designs which utilize a pivoting transducer assembly, the preferred probe 101 performs scanning motion using a sweep mechanism (including probe electronics 118 and a reciprocating motor 127) to rotate the fiber acoustic waveguide 107 about the longitudinal axis 119. The fiber acoustic waveguide 107 directly contacts the transducer 117 at a first end 116 and conveys ultrasound between the transducer and a second end 120 of the waveguide, which is adjacent to the radome 113, and which mounts a deflector 149. It is the reciprocal rotation of the deflector 149 about the longitudinal axis 119 that causes imaging waves to be distributed in a scanning motion. Consequently, the oblong nose 109 does not require substantial thickness (as indicated by reference arrows 121), and may be made practically as narrow as desired for the purposes of accessing hard-to-reach locations. Since oscillatory, scanning motion of the cladded waveguide 107 and the transducer 117 occurs as "to-and-fro" rotational motion about the longitudinal axis 119, inertia considerations are also reduced. Finally, since the waveguide 107 and transducer 117 are not continually rotated in one direction, but rather, are oscillated "to-and-fro" in opposite rotational directions, the transducer 117 and probe electronics 118 do not require a commutator arrangement for electrical connection; rather, the transducer is coupled to the probe electronics by a flexible circuit based on an insulating material.

Since the transducer 117 is mounted within the cylindrical main body 105, the sizing of the body 105 is not critical, and a high frequency transducer may be used with appropriate solid backing to prevent damage to the transducer during its rotation. This construction advantageously permits the production of nearly any desired frequency of ultrasound; optimal production of ultrasound by each transducer having thickness "t" is described by the relation $$f = v_t/2t, \tag{1}$$

where $v_t$ is the velocity of the ultrasound in the transducer material (PZT). Ultrasound produced by the probe 101 may be electronically varied within a small range for a given transducer, and multiple, alternate transducers may be included for switching between a wider range of ultrasound frequencies. In the preferred probe 101, however, the ultrasonic transducer 117 may be selected to produce ultrasound having very high frequencies, generally at about 50–100 megahertz, and multiple transducers may be cascaded at the first end 116 of the waveguide to permit switching between different ultrasound frequencies. Appropriate high frequency transducers for use in the present application are disclosed in U.S. Pat. No. 5,291,090, which is hereby incorporated by reference.

With reference to FIG. 2, the construction of the handheld probe 101 will be described in greater detail. An electronic cable 123 provides transducer electronics 118 with (1) a pulsed ultrasound input signal, which directs production of ultrasound by the transducer 117; (2) a power supply signal 124, for operating the reciprocating motor 127 that rotates the waveguide about its longitudinal axis 119; and (3) a return signal, which carries image information used to generate a visual display of the section 115. The latter signal is configured by the probe electronics to include both a frame sync signal 128 which is generated by an angle encoder 129 of the sweep mechanism, as well as an image output signal 131 which is output by the transducer 117 at times when the transducer 117 is used for ultrasound detection.

Figure 4:
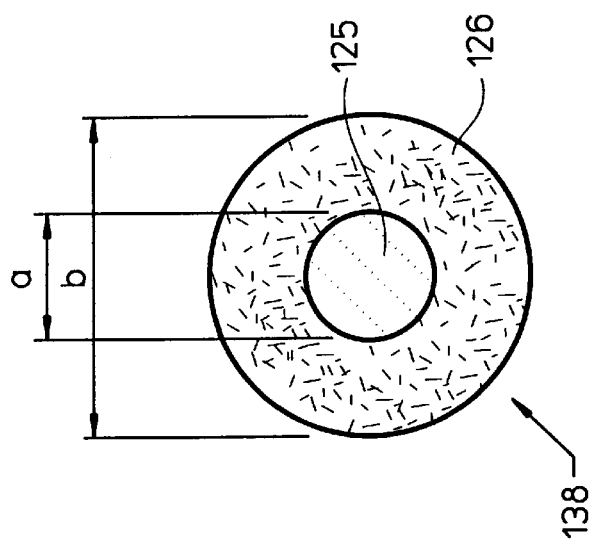
FIG. 4 is a cross-section of a cladded acoustic fiber used in the scanner of FIGS. 2 and 3, taken across line 4—4 of FIG. 3.

The cylindrical main body 103 is made of a hard plastic exterior, and includes a mounting 133 which, in addition to the motor 127, constrains the fiber acoustic waveguide to reciprocally rotate about the longitudinal axis 119. As seen in FIG. 4, the fiber acoustic waveguide 107 is a circular symmetric cladded fiber 138 having a fused quartz 3% germanium doped core layer 125 of diameter "a" (which transmits the ultrasound), and a relatively thick fused quartz cladding layer 126 of diameter "b." A cladded fiber is used to substantially eliminate loss through an outer periphery of the core layer 125, except at the second end 120 of the fiber, where ultrasound is deflected away from the longitudinal axis 119. Importantly, the core layer 125 is expected to be between 250- and 500-microns in thickness, whereas the cladding layer 126 should be made as thick as practical, such that the overall diameter of the fiber "b" is at least four times as great as the diameter "a" of the core. Preferably, the fiber 138 is selected such that the diameter "b" is at least five times as great as the diameter "a" of the core. Notably, although fused quartz is the presently prefered fiber material, other suitable materials can be used, such as a metal or sapphire core. In fact, a suitable sapphire fiber core having a suitable cladding and a medical grade polyester cladding should be obtainable from Saphikon Inc., of Milford, N.H.

Returning again to FIG. 2, the fiber acoustic waveguide 107 extends from the main cylindrical body 105 to an interface 135, where the oblong nose 109 screws on to the main cylindrical body. At this interface 135, the waveguide 107 terminates in a coupling 137, which mates with a coupling 139 of the oblong nose 109. In this manner, various configurations of the main cylindrical body 105 and the oblong nose 109 may be made interchangeable, enabling a variety of different fittings to be used in multiple applications.

The oblong nose 109 includes a continuation 141 of the fiber acoustic waveguide 107, which conveys ultrasound to a distal end "D" of the probe. The continuation 141 receives ultrasound from the transducer 117 via the couplings 137 and 139, and extends through a gasket 143 into the coupling media 111. A series of supports 145 retains the waveguide in the approximate center of the oblong nose, and the gasket 143 prevents leakage of the coupling media 111 (i.e., coupling fluid) from the distal end "D" of the probe. The coupling fluid permits the fiber acoustic waveguide 107 to be reciprocally rotated (i.e., oscillated, as indicated by arrows 150), yet minimizes the effect of the rotation upon ultrasound propagation through the coupling media 111 and the radome 113. The oblong nose 109 is seen in FIG. 2 to be slightly curved, and the waveguide may be made flexible to accommodate such bending as appropriate for the particular application.

Figure 3:
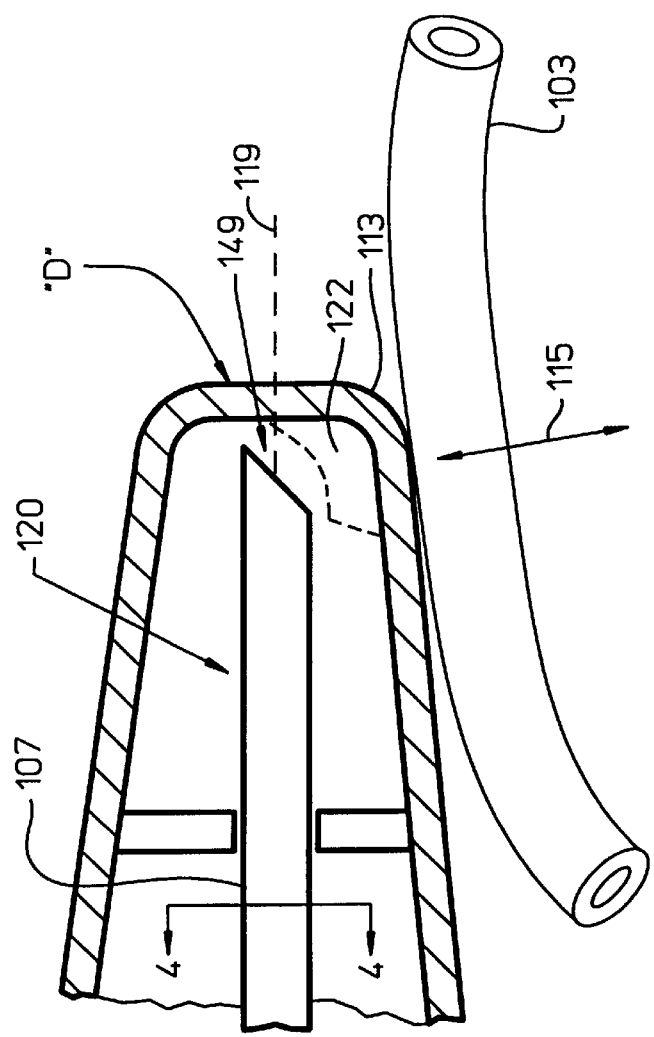
FIG. 3 is a close-up of a distal end of the scanner of FIG. 2, indicated by the reference arrow "D" of FIG. 2.

FIG. 3 shows a close-up of the distal end "D" of the probe and of the second end 120 of the fiber acoustic waveguide 107. As seen in FIG. 3, the second end 120 is angled to form the deflector 149, to redirect ultrasound between the section 115 of the object 103 and the waveguide's longitudinal axis 119. The term "deflector" indicates that ultrasound is redirected in the physical sense, meaning that it encompasses refraction of ultrasound, which is actually the physical condition occurring at the second end 120 of the waveguide 107. Not only does the deflector 149 divert ultrasound between the waveguide's longitudinal (transmission) axis and the section 115, but in combination with the reciprocal motion of the fiber acoustic waveguide 107, the reflector is effective to distribute ultrasound in scanning motion, much like the raster of a television set, to facilitate generation of a video or similar format of visual display. A solid material may also be used as a lens 122, to converge or diverge ultrasound traveling between the radome 113 and the deflector 149. In this regard, the deflector 149 may also be made parabolic concave or convex to also converge or diverge ultrasound, the deflector is seen to be substantially planar, as seen in FIG. 3.

The scanning motion is seen to sweep a sector 151 in FIG. 5, which shows a cross-section of the probe 101 of FIG. 2, taken across lines 5—5 of FIG. 2. In particular, FIG. 5 shows the cylindrical main body 103 of the probe, as well as the oblong nose 109 and the radome 113. As indicated by FIG. 5, oscillatory motion of the fiber acoustic waveguide 107 (and the deflector 149) causes imaging waves and reflected imaging waves to sweep a sector within the object 103, as indicated by the reference numeral 116. Preferably, the angular width of the sector is made electronically variable via a control knob 153, which modifies the power supply signal 124 (FIG. 2) for increasing or decreasing the magnitude of reciprocal rotation provided by the motor 127. In this manner, the resolution of specific features within the generated image of the section 115 may be enhanced by increasing the signal-to-noise ratio by focussing the sector scan to only image a region of interest.

What has been described is a novel hand-held probe 101 that is useful in a wide range of applications, particularly in invasive medical procedures, such as open heart surgery. Use of an oblong nose, such as the nose 109 seen in the accompanying drawings, facilitates access to remote tissue areas, for example, for use during brain surgery as previously alluded. In addition, the interchangeable nature of the main cylindrical body 105 and the oblong nose 109 facilitates use of replaceable parts, thus minimizing possibility of contagion. Finally, since the main cylindrical body 105 is mounted away from a direct contact area of the probe, different or multiple transducers may be used, thereby enabling production of a wide range of ultrasonic frequencies (when ultrasound is used for the imaging waves). Alternatively, multiple transducers may be used in a single probe, such that ultrasound frequency may be more readily varied during a procedure. As can be seen from the above description, the preferred probe provides a safer scanner that may be used in a wide variety of applications, particularly in intraoperative procedures.

Having thus described an exemplary embodiment of the invention, it will be apparent that further alterations, modifications, and improvements will also occur to those skilled in the art. Further, it will be apparent that the present invention is not limited to the specific form of an ultrasound device, as described above, nor just to the field of surgery or medical procedures. Rather, the preferred probe, and the invention in general, may be applied to a wide variety of applications. Various alterations, modifications, and improvements, though not expressly described or mentioned above, are nonetheless intended and implied to be within the spirit and scope of the invention. Accordingly, the foregoing discussion is intended to be illustrative only; the invention is limited and defined only by the various following claims and equivalents thereto.

What is claimed is:

1. A method of imaging an object using a direct contact ultrasound scanner comprised of an ultrasound imaging mechanism that produces ultrasonic imaging waves, a radome adapted to directly contact the exterior surface of the object and permit passage of imaging waves between the scanner and the object, a waveguide having a transmission axis, a first end contacting the ultrasound imaging mechanism and a second end extending into a coupling medium that is contained by the radome and isolated from the ultrasound imaging mechanism, said method comprising:

a. while holding the scanner in one hand, manipulating the scanner with the one hand to move the radome into direct contact with an external surface of the object;

b. generating ultrasonic imaging waves using the imaging mechanism;

c. conveying the ultrasonic imaging waves from the imaging mechanism to the object by passing the imaging waves through the waveguide into the coupling medium and out to the object through the radome;

d. conveying reflected ultrasonic imaging waves from the object to the ultrasound imaging mechanism using the radome, the coupling media and the waveguide; and e. using the ultrasound imaging mechanism to generate an electronic image signal from the reflected ultrasonic imaging waves received from the object.

2. The method of claim 1, wherein:
i. the direct contact ultrasound scanner further comprises a sweep mechanism coupled to the waveguide and isolated from the coupling medium and a deflector coupled to the second end of the waveguide;
ii. in step d, the deflector deflects the reflected ultrasonic imaging waves from the object into the waveguide along the transmission axis and the sweep mechanism rotates both the waveguide and the deflector, so that the reflected ultrasonic imaging waves directed into the waveguide encompass a sweep sector having an angular width; and
iii. in step e, the electrical image signal is isolated from the coupling medium.

3. The method of claim 2, wherein the scanner further comprises an angle encoder that generates a synchronization signal for the electronic image signal in step e.

4. The method of claim 2, wherein the scanner further comprises a sector control mechanism that varies the angular width of the sweep sector in step d.

5. The method of claim 2, wherein in step d, the sweep mechanism rotates the waveguide in an oscillatory fashion and the waveguide is rotated less than 360° between two angular positions.

6. The method of claim 1, wherein:
i. the ultrasound imaging mechanism is an ultrasound transducer and the scanner further comprises control electronics coupled to the ultrasound transducer; and
ii. the control electronics cause the transducer to produce ultrasound in discrete bursts, to detect the reflected imaging waves when ultrasound is not being produced by the transducer, and to responsively produce the electronic image signal.

7. A direct contact ultrasound scanner for use in scanning an object through direct contact with the object's exterior, comprising:
a. an ultrasound transducer which is excited by electrical signals;
b. a coupling medium;
c. a direct contact area which is transparent to ultrasound and provides an interface between the coupling medium and the exterior of the object;
d. an ultrasound waveguide having a transmission axis, a first end that contacts the transducer and a second end that extends into the coupling medium; and
e. a sweep mechanism connected to the waveguide and capable of rotating the waveguide in a manner to sweep a section having an angular width that encompasses at least a portion of the object
wherein:
the ultrasound transducer is isolated from the direct contact area and out of direct electrical contact with the coupling medium; and wherein the scanner is adapted to be held in one hand while being operated by the one hand to bring the direct contact area into direct contact with an external surface of an object.

8. The direct contact ultrasound scanner of claim 7, further comprising a deflector, connected to the second end of the waveguide, that redirects ultrasound between the section defined by the sweep of the waveguide and the transmission of the axis of the waveguide; wherein:
i. the entire waveguide and the deflector are rotationally moved about the transmission axis by the sweep mechanism; and
ii. the sweep mechanism and the ultrasound transducer are both insulated from the coupling medium.

9. The direct contact ultrasound scanner of claim 8, wherein the deflector comprises an angular termination of the second end of the waveguide.

10. The direct contact external ultrasound scanner of claim 7, wherein the waveguide is a cladded fiber acoustic waveguide having a core portion and a cladding portion.

11. The direct contact ultrasound scanner of claim 10, wherein the cladding portion has a thickness such that the cladded fiber acoustic waveguide has a diameter at least four times the predetermined diameter.

12. The direct contact ultrasound scanner of claim 10, wherein the core portion is made of doped fused quartz, and the cladding portion is made of fused quartz.

13. The direct contact ultrasound scanner of claim 10, wherein the core portion and the cladding portion are each made of a silicate material.

14. The direct contact ultrasound scanner of claim 10, wherein the core portion is made of a metal material.

15. The direct contact ultrasound scanner of claim 10, wherein the core portion is made of a sapphire material.

16. The direct contact ultrasound scanner of claim 7, further comprising a sector control mechanism that selectively varies the angular width of the sweep of the waveguide to define a sector being imaged within the section.

17. The direct contact ultrasound scanner of claim 7, wherein:
i. the coupling media is a liquid that transmits ultrasound;
ii. the waveguide is a solid material; and
iii. the direct contact area is a radome that is transparent to ultrasound and retains the liquid within the scanner.

18. The direct contact ultrasound scanner of claim 17, wherein said scanner further comprises electronics that cause the ultrasound transducer to produce outgoing ultrasound imaging waves in discrete bursts, to detect reflected imaging waves returning from the object when the ultrasound transducer is not producing outgoing ultrasound imaging waves; and to produce an image output signal in response to the reflected incoming ultrasound imaging waves.

19. The direct contact ultrasound scanner of claim 7, wherein the transducer produces ultrasound of frequencies greater than about 50 megahertz.

20. The direct contact ultrasound scanner of claim 7, wherein the waveguide has a diameter of at least two millimeters.

21. The direct contact ultrasound scanner of claim 7, the direct contact ultrasound scanner further comprising a main body and a nose extending outward from the main body, wherein:
i. the main body contains the transducer and substantially all electronic signals;
ii. the nose is curved and mounted to the scanner surface on a convex side of the nose, defining a plane of contact with the object that is tangential to the curve of the nose and providing for the object to be scanned with substantially flat contact between the scanner surface and the object, notwithstanding that the main body is located above the plane of contact; and
iii. the waveguide is mounted substantially within the nose, permitting conveyance of ultrasound between the scanner surface and the transducer via the waveguide notwithstanding bending and rotation of the waveguide.

* * * * *